(12) United States Patent
Swanson et al.

(10) Patent No.: US 8,673,372 B2
(45) Date of Patent: *Mar. 18, 2014

(54) METHODS FOR IMPROVING THE APPEARANCE OF HYPERPIGMENTED SKIN USING A SYNERGISTIC COMPOSITION COMPRISING BANYAN TREE, LOTUS, AND CLOVER SERUM FRACTIONS

(75) Inventors: Cheri Lynn Swanson, West Chester, OH (US); Leo Timothy Laughlin, II, Mason, OH (US); Deborah Ruth Finlay, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/402,608

(22) Filed: Feb. 22, 2012

(65) Prior Publication Data

US 2012/0237459 A1 Sep. 20, 2012

Related U.S. Application Data

(60) Provisional application No. 61/445,487, filed on Feb. 22, 2011.

(51) Int. Cl.
*A61K 36/00* (2006.01)
*A61K 8/00* (2006.01)

(52) U.S. Cl.
USPC ........................................ 424/725; 424/401

(58) Field of Classification Search
USPC .................................................. 424/401, 725
See application file for complete search history.

(56) References Cited

U.S. PATENT DOCUMENTS

| | | | |
|---|---|---|---|
| 3,755,560 | A | 8/1973 | Dickert |
| 4,421,769 | A | 12/1983 | Dixon |
| 6,468,564 | B1 | 10/2002 | Riley |
| 7,442,391 | B2 | 10/2008 | Koganov |
| 2003/0175235 | A1* | 9/2003 | Koganov ................... 424/74 |
| 2004/0175347 | A1 | 9/2004 | Bissett |
| 2006/0269111 | A1* | 11/2006 | Stoecker et al. ............. 382/128 |
| 2006/0275237 | A1 | 12/2006 | Bissett |
| 2007/0116696 | A1* | 5/2007 | Riley ......................... 424/94.5 |
| 2008/0206373 | A1 | 8/2008 | Millikin |
| 2012/0201768 | A1 | 8/2012 | Swanson |
| 2012/0237459 | A1 | 9/2012 | Swanson |
| 2012/0237460 | A1 | 9/2012 | Swanson |

FOREIGN PATENT DOCUMENTS

| | | |
|---|---|---|
| DE | 10329004 | 1/2005 |
| EP | 1344516 A1 | 9/2003 |
| JP | 2003048846 A * | 2/2003 |
| JP | 2008184416 A * | 8/2008 |
| JP | 2008184440 A * | 8/2008 |
| WO | 02087533 A1 | 11/2002 |
| WO | 2005041996 A1 | 5/2005 |

OTHER PUBLICATIONS

Gao et al. Efficacy and Safety of Innovative Cosmeceuticals, Clinics in Dermatology (2008) 26, 367-374.*
Gilchrest BA et al. Mechanism of Ultraviolet Light-Induced Pigmentation, Photochem Photobiol. Jan. 1996;63(1):1-10.*
U.S. Appl. No. 13/402,677, filed Feb. 22, 2012, Cheri Lynn Swanson, et al.
Kovali, Michael. Claudins—Key Pieces in the Tight Junction Puzzle. Cell Communication and Adhesion. 13:127-138, 2006.
Chikuma M "Aquaporin-3 functions as a glycerol transporter in mammalian skin," Hara-, Biol Cell. Jul. 2005;97(7):479-86.
Hara-Chikuma "Roles of Aquaporin-3 in the Epidermis", M., J Invest Dermatol. Sep. 2008;128(9):2145-51. Epub Jun. 12, 2008.
Hara, "Glycerol replacement corrects defective skin hydration, elasticity, and barrier function in aqaporin-3-deficient mice,", Proc Natl Acad Sci U S A. Jun. 10, 2003;100(12):7360-5. Epub May 27, 2003.

* cited by examiner

*Primary Examiner* — Michael G Hartley
*Assistant Examiner* — Nabila Ebrahim
(74) *Attorney, Agent, or Firm* — John G. Powell

(57) ABSTRACT

A method of improving the appearance of a hyperpigmented spot may comprise the step of applying a composition comprising an effective amount of banyan tree serum fraction, lotus serum fraction, and clover serum fraction to a hyperpigmented spot on a skin surface, wherein the composition is applied for a period of time sufficient to improve the appearance of the hyperpigmented spot. The method may include the step of identifying a hyperpigmented spot on a facial skin surface. Other methods as disclosed include a method for improving the appearance of post-inflammatory hyperpigmentation.

29 Claims, No Drawings

METHODS FOR IMPROVING THE APPEARANCE OF HYPERPIGMENTED SKIN USING A SYNERGISTIC COMPOSITION COMPRISING BANYAN TREE, LOTUS, AND CLOVER SERUM FRACTIONS

CROSS REFERENCE TO RELATED APPLICATION

This application claims the benefit of U.S. Provisional Application No. 61/445,487, filed Feb. 22, 2011.

FIELD OF THE INVENTION

The present invention relates to methods for improving the appearance of hyperpigmented mammalian skin using a synergistic composition comprising banyan tree, lotus, and clover serum fractions.

BACKGROUND OF THE INVENTION

Human skin comprises three principal layers: the epidermis, the dermis, and the subcutaneous fat layer. The epidermis comprises four layers (from top to bottom): the stratum corneum, the granular layer, the spiny layer, and the basal layer. A separate fifth layer, the stratum lucidum, may be present between the stratum corneum and granular layer. The basal layer produces cells which gradually migrate upward to form the other epidermal layers. As these cells migrate upward, they lose their central nucleus and start to produce skin proteins (keratins) and fats (lipids). These cells are identified as keratinocytes when present in the upper layers of the epidermis. Melanocytes are another class of cells located in the basal layer of the epidermis. Melanocytes are responsible for the production of melanin, which is a primary factor in skin pigmentation.

Melanin is produced by a complex set of reactions within the melanocyte involving, at a basic level, the enzyme tyrosinase and L-tyrosine as a substrate. Tyrosinase catalyzes the conversion of L-tyrosine to DOPA (L-3,4-dihydroxyphenylalanine) and of DOPA to dopaquinone. Dopaquinone undergoes further conversion to form melanin. Melanin aggregates in organelles known as the melanosomes which are transferred to keratinocytes along slender filaments of the melanocyte known as dendrites. There are approximately 1500 gene products expressed in melanosomes with 600 of them being expressed at any given time and 100 of them believed to be unique to the melanosome. In addition, there are many regulatory elements involved in signaling, in the transport of melanosomes within the melanocyte, and in the transfer of melanosomes to the keratinocytes.

The production of melanin can be triggered by a variety of external and internal events. For example, melanocytes produce additional melanin when skin is subjected to UV radiation. The melanin is then transported via melanasomes to the keratinocytes, which then leaves the skin with a "tanned" appearance. Once the UV light is removed the melanocytes return to normal levels of melanin production. Inflammation may initiate hyperpigmentation by direct stimulation of the melanocytes by mediators such as IL-1, endothelin-1, and/or stem cell factor. Reactive oxygen species, such as superoxide and nitric oxide, generated in damaged skin or released as by-products from inflammatory cells may be stimulators of melanocytes.

Over time, chronic UV exposure and other intrinsic and extrinsic aging factors may lead to permanent gene expression changes in keratinocytes and/or melanocytes resulting in age-related hyperpigmented spots. The mRNA levels of some melanogenesis associated genes (for example, tyrosinase, TYRP1) are reported to be increased in actinic lentigos (age spots). There may also be accentuation of the epidermal endothelin cascade and a role for stem cell factor in hyperpigmentation. These changes can result in overproduction of melanin and resultant hyperpigmented spots that persist even when an insult, such as UV exposure, is avoided.

Even beyond hyperpigmented spots, chronic UV exposure and other intrinsic and extrinsic aging factors may lead to more subtle changes in skin tone. Often these changes are described as uneven tone or as a mottled appearance.

Age spots and hyperpigmented skin tone can add several years of perceived age to an individual. Thus, there is a continuing desire to provide compositions and methods of treatment that can improve the appearance of hyperpigmented spots and overall skin tone.

SUMMARY OF THE INVENTION

A method of improving the appearance of hyperpigmented skin tone comprising the step of applying a first composition comprising an effective amount of banyan tree serum fraction, lotus serum fraction, and red clover serum fraction blend to an area of hyperpigmented skin, wherein the composition is applied for a period of time sufficient to improve the appearance of the hyperpigmented skin.

A method of improving the appearance of a hyperpigmented spot comprising the step of applying a first composition comprising an effective amount of banyan tree serum fraction, lotus serum fraction, and red clover serum fraction blend to a hyperpigmented spot on a skin surface, wherein the composition is applied for a period of time sufficient to improve the appearance of the hyperpigmented spot.

A method of improving the appearance of a hyperpigmented spot comprising the steps of (a) identifying a hyperpigmented spot on a facial skin surface and (b) applying a composition comprising an effective amount of banyan tree serum fraction, lotus serum fraction, and red clover serum fraction blend to the hyperpigmented spot on the facial skin surface, wherein the composition is applied for a period of time sufficient to improve the appearance of the hyperpigmented spot.

A method of improving the appearance of post-inflammatory hyperpigmentation, the method comprising the steps of (a) identifying an area of post-inflammatory hyperpigmentation on a skin surface; (b) applying to the area an effective amount of banyan tree serum fraction, lotus serum fraction, and red clover serum fraction blend, wherein the composition is applied at least daily for a period of time sufficient to improve the appearance of the area of post-inflammatory hyperpigmentation; and (c) applying to the area an effective amount of an anti-inflammatory agent.

In response to the technical problems identified in the background, the present invention may take other forms. Further forms of the present invention will be appreciated in the detailed description that follows.

DETAILED DESCRIPTION OF THE INVENTION

All percentages and ratios used herein are by weight of the total composition and all measurements made are at 25° C., unless otherwise designated. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "apply" or "application" as used in reference to a composition, means to apply or spread the compositions of the present invention onto a human skin surface such as the epidermis.

The term "dermatologically acceptable" as used herein means that the compositions or components described are suitable for use in contact with human skin tissue without undue toxicity, incompatibility, instability, allergic response, and the like.

The term "effective amount" as used herein means an amount of a compound or composition sufficient to significantly induce a positive benefit.

The term "post-inflammatory hyperpigmentation" as used herein refers to an acute to chronic increase in pigmentation as a response to a transient inflammatory event. Post-inflammatory hyperpigmentation is particularly prevalent in, but not limited to, dark skin subjects. Post-inflammatory hyperpigmentation typically subsides once the transient inflammatory event dissipates. Examples of transient inflammatory events include, but are not limited to, acne lesions, ingrown hairs, scratches, insect bites, surfactant damage, and short-term UV exposure.

The term "hyperpigmented spot" as used herein refers to a defined area of skin wherein the pigmentation is greater than that of an adjacent area of skin due to localized and chronic or systemic overproduction of melanin. Hyperpigmented spots typically are between about 2 mm and about 10 mm in diameter but smaller or larger spots are possible. Hyperpigmented spots can include one or more of age spots, sun spots, solar lentigos, hypo-melanotic lesions, freckles, and melasma spots.

The term "age spots" as used herein refers to a hyperpigmented spot wherein the pigmentation is due to localized and chronic overproduction of melanin caused by intrinsic or extrinsic aging factors.

The term "skin tone agent" as used herein refers to an agent that regulates melanin production signals, synthesis of melanin, systemic transfer of melanin between the melanocyte and the keratinocyte, and/or melanin degradation. Skin tone agents can improve the appearance of uneven skin tone by acting as a lightening or pigmentation reduction cosmetic agent.

The term "skin tone" as used herein refers to the overall appearance of melanin in the skin caused by the systemic, rather than transient, synthesis of melanin. Skin tone is typically characterized over a larger area of the skin. The area ideally may be than 100 $mm^2$, but larger areas are envisioned such as the entirety of the facial skin or any of the facial skin surfaces. Skin tone can be measured by image analysis. For example, overall lightness can be measured by L* coordinate in L*a*b* color space (International Commission on Illumination). Chromophore mapping such as melanin mapping and melanin concentration may be used as an indicator of overall skin tone. Mean melanin may be calculated from the chromophore map data. Additionally, skin tone evenness can be determined by melanin evenness which also may be calculated from the chromophore map data. Suitable chromophore mapping techniques are discussed in the example below.

The term "facial skin surface" as used herein refers to one or more of forehead, periorbital, cheek, perioral, chin, and nose skin surfaces.

As used herein, "exogenous solvent" means any solvent that is not inherently present in the plant material, but is placed in contact with the plant material for the purpose of separating (e.g., extracting) compounds from the plant material.

I. Compositions

The present invention relates to various compositions and, more specifically, to compositions for application to a skin surface. The compositions may be in a wide variety of product forms that include, but are not limited to, solutions, suspensions, lotions, creams, gels, toners, sticks, pencil, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks (with and without insoluble sheet), make-up such as foundations, eye liners, and eye shadows, and the like. The composition form may follow from the particular dermatologically acceptable carrier chosen, if present in the composition.

A. Serum Fractions

Compositions of the present invention comprise effective amounts of banyan tree serum fraction, lotus serum fraction, and clover serum fraction. As demonstrated by Example 2 below, Applicant has surprisingly found that the combination of these three serum fractions results in a synergistic mixture that inhibits the synthesis of melanin, thereby improving the appearance of skin hyperpigmentation, to a much greater degree than what would be expected from the additive effects of each component separately.

In Example 2a, the % melanin synthesis inhibition of the individual banyan tree, clover, and lotus serum fractions, respectively, was measured as 42%, 16%, and 1%. Thus, one would expect that the additive effect of all three serum fractions in a blend would result in 59% melanin synthesis inhibition (42%+16%+1%=59%). However, the actual serum fraction blend surprisingly resulted in 100% melanin synthesis inhibition, which was 41% greater than expected (100%−59%=41% more than expected).

In Example 2b, the melanin synthesis inhibition assay was repeated at serum fraction concentration levels that were one-half those in Example 2a. Again, the serum fraction combination resulted in a much greater % melanin synthesis inhibition than what one would have expected from the sum of the individual serum fraction results. Here, the % melanin synthesis inhibition of the individual banyan tree, clover, and lotus serum fractions, respectively, was measured as 0%, 14%, and 7%. The sum of these three results is 21% (0%+14%+7%=21%). The actual serum fraction blend resulted in 63% melanin synthesis inhibition, which was 42% greater than expected from the sum (63%−21%=42%).

Banyan tree, lotus, and clover serum fractions consist essentially of the flower, leaf, and stem serum fractions obtained from *Ficus Benghalensis, Nelumbo Nucifera*, and *Trifolium Pratense*, respectively. The preferred serum fractions are produced by Integrated Botanical Technologies, LLC, of Ossining, N.Y., USA, under the trade names *Ficus Bengalensis* Enriched Serum Fraction™ (INCI Name: *Ficus Indica* Flower/Leaf/Stem Juice), Lotus Enriched Serum Fraction™ (INCI Name: *Nelumbo Nucifera* Flower/Leaf/Stem Juice), and Red Clover Enriched Serum Fraction™ (INCI Name: *Trifolium Pratense* (Clover) Flower/Leaf/Stem Juice).

In some embodiments, the composition may comprise banyan tree serum fraction in an amount of from 0.001% to 15%, alternatively from 0.002% to 10%, alternately from 0.025% to 10%, in other embodiments from 0.05% to 10%, in others from 0.05% to 5%, and in others from 0.1% to 5%, by weight of the total composition. The composition may comprise lotus serum fraction in an amount of from 0.001% to 15%, alternatively from 0.002% to 10%, alternatively from 0.01% to 15%, alternately from 0.025% to 10%, in other embodiments from 0.05% to 10%, in others from 0.05% to 5%, and in others from 0.1% to 5%, by weight of the total composition. The composition may comprise clover serum fraction in an amount of from 0.001% to 15%, alternatively from 0.002% to 10%, alternatively from 0.01% to 15%, alternately from 0.025% to 10%, in other embodiments from 0.05% to 10%, in others from 0.05% to 5%, and in others from 0.1% to 5%, by weight of the total composition.

The method for making a serum fraction comprises the steps of: (a) separating cell juice from clean, fresh, un-wilted plant matter to obtain fresh cell juice, wherein no exogenous liquid is added prior or during said separating; (b) filtering said fresh cell juice to obtain fiber-free cell juice; and (c) fractionating said fiber-free cell juice to obtain the serum fraction for use herein. Suitable serum fraction preparation methods are set forth in U.S. Pat. No. 7,442,391, "Bioactive Botanical Cosmetic Compositions and Processes for their Production," to Koganov, and in co-pending U.S. Provisional Application Ser. No. 61/381,748, filed 10 Sep. 2010 by Swanson et al.

The resulting serum fractions have superior bioactivity versus traditionally prepared plant extracts. Unlike traditional extracts, the serum fraction is prepared from fresh plant cell juice that has been mechanically separated from the rest of the fresh plant material. Importantly, no exogenous solvent (e.g., water, hexane, acetone, ethanol) is added during the juice separation process. The resulting cell juice contains the full spectrum of compounds found in fresh plant matter, thus the resulting serum fractions contain a much broader range of active compounds than do traditional plant extracts, which contain only the narrow range of compounds that can be separated with a particular solvent.

Furthermore, using fresh plants maintains the integrity of the bioactive components inherently present in the fresh plant matter. Traditional plant extracts are not prepared from fresh plant matter, but rather from dried plant material, which has undergone degradation due to dehydration. During dehydration, the cell walls are compromised, causing the degradation of compounds through mechanisms such as hydrolysis, oxidation, polymerization, Maillard reactions, and isomerization. When the dried leaves are extracted, the resulting extract thus contains these degradation products that were not originally present in the fresh plant matter. Accordingly, the composition of the resulting dry leaf extract greatly differs from that of fresh juice and the resulting serum fraction.

B. Skin Tone Agent

In some embodiments, it may be desirable to include a skin tone agent in the composition. The skin tone agents can be included to further improve overall skin tone. When present, the compositions of the present invention contain up to about 50%, 40%, 30%, 20%, 10%, 5%, or 3%, by weight of the composition, of the skin tone agent. When present, the compositions of the present invention contain at least about 0.001%, 0.01%, 0.1%, 0.2%, 0.5%, or 1%, by weight of the composition, of the skin tone agent. Suitable ranges include any combination of the lower and upper limits including suitable ranges from about 0.1% to about 50%; from about 0.2% to about 20%; or from about 1% to about 10%, by weight of the composition, of the skin tone agent. The amounts listed herein are only to be used as a guide, as the optimum amount of the skin tone agent will depend on the specific active selected since their potency does vary considerably.

Suitable skin tone agents include, but are not limited to, sugar amines, vitamin B3 compounds, arbutin, deoxyarbutin, 1,3-dihydroxy-4-alkylbenzene such as hexylresorcinol, sucrose dilaurante, bakuchoil (4-[(1E,3S)-3-ethenyl-3,7-dimethyl-1,6 octadienyl]phenol or monterpene phenol), pyrenoine (available from Biotech Marine, France), panicum miliaceum seed extract, arlatone dioic acid, cinnamic acid, ferulic acid, achromaxyl, methyl nicotinamide, oil soluble licorice extract, folic acid, undecylenic acid (i.e., undecenoic acid), zinc undecylenate, thiamine (Vitamin B1) and its hydrochloride, L-tryptophan, *helianthus annuus* (sunflower) and *vitis vinifera* (grape) leaf extract, carnosine (i.e., dragosine), methyl gentisate, 1,2-hexandiol and 1,2-octandiol (i.e., combination sold as Symdiol 68 by Symrise AG, Germany), inositol, decylenoylphenylalanine (e.g., sold under the tradename Sepiwhite by Seppic, France), koijic acid, hexamidine compounds, salicylic acid, and retinoids including retinol and retinyl propionate.

In certain embodiments, the additional skin tone agent is selected from vitamin B3 compounds, sugar amines, hexamidine compounds, salicylic acid, 1,3-dihydroxy-4-alkylbenzene such as hexylresorcinol, and retinoids. As used herein, "vitamin $B_3$ compound" means a compound having the formula:

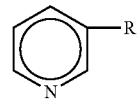

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. As used herein, "sugar amine" includes isomers and tautomers of such and its salts (e.g., HCl salt) and its derivatives. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). As used herein, "hexaminide compound" means a compound having the formula.

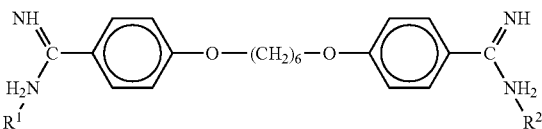

wherein $R^1$ and $R^2$ are optional or are organic acids (e.g., sulfonic acids, etc.). In one embodiment, hexamidine compound is hexamidine diisethionate.

C. Anti-Inflammatory Agents

Hyperpigmentation may result from skin inflammation. Transient inflammatory events triggering hyperpigmentation and, more specifically, post-inflammatory hyperpigmentation include, but are not limited to, acne lesions, ingrown hairs, scratches, insect bites, surfactant damage, allergens, and short-term UV exposure. Inflammation induced hyperpigmentation including post-inflammatory hyperpigmentation may be managed by incorporating into the compositions of the present invention an anti-inflammatory agent. When present, the compositions of the present invention contain up to about 20%, 10%, 5%, 3%, or 1% by weight of the composition, of the anti-inflammatory agent. When present, the compositions of the present invention contain at least about 0.001%, 0.01%, 0.1%, 0.2%, 0.3%, 0.5%, or 1%, by weight of the composition, of the anti-inflammatory agent. Suitable ranges include any combination of the lower and upper limits Suitable anti-inflammatory agents include, but are not limited to nonsteroidal anti-inflammatory agents (NSAIDS including but not limited to ibuprofen, naproxen, flufenamic acid, etofenamate, aspirin, mefenamic acid, meclofenamic acid, piroxicam and felbinac), glycyrrhizic acid (also known as glycyrrhizin, glycyrrhixinic acid, and glycyrrhetinic acid glycoside) and salts such as dipotassium glycyrrhizate, glycyrrhetenic acid, licorice extracts, bisabolol (e.g., alpha bisabolol), manjistha (extracted from plants in the genus *Rubia*, particularly *Rubia cordifolia*), and guggal (extracted from plants in the genus *Commiphora*, particularly *Commiphora mukul*), kola extract, chamomile, and sea whip extract (extracts from plant in the order Gorgonacea), derivatives of any of the foregoing, and mixtures thereof.

D. Sunscreen Actives

The compositions of the subject invention may comprise one or more sunscreen actives (or sunscreen agents) and/or ultraviolet light absorbers. Herein, "sunscreen active" collectively includes sunscreen actives, sunscreen agents, and/or ultraviolet light absorbers. Sunscreen actives include both sunscreen agents and physical sunblocks. Sunscreen actives may be organic or inorganic. Examples of suitable sunscreen actives are disclosed in Personal Care Product Council's *International Cosmetic Ingredient Dictionary and Handbook*, Thirteenth Edition, as "sunscreen agents." Particularly suitable sunscreen actives are 2-ethylhexyl-p-methoxycinnamate (commercially available as PARSOL™ MCX), 4,4'-t-butyl methoxydibenzoyl-methane (commercially available as PARSOL™ 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, menthyl anthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, benzylidene camphor and derivatives thereof, titanium dioxide, and mixtures thereof.

In one embodiment, the composition may comprise from about 1% to about 20%, and alternatively from about 2% to about 10% by weight of the composition, of the sunscreen active. Exact amounts will vary depending upon the chosen sunscreen active and the desired Sun Protection Factor (SPF), which is within the knowledge of one of skilled in the art.

E. Optional Components

The compositions of the present invention may contain a variety of other ingredients provided that they do not unacceptably alter the benefits of the invention. When present, compositions of the present invention may contain from about 0.0001% to about 50%; from about 0.001% to about 20%; or, alternately, from about 0.01% to about 10%, by weight of the composition, of the optional components. The amounts listed herein are only to be used as a guide, as the optimum amount of the optional components used in a composition will depend on the specific active selected since their potency does vary considerably. Hence, the amount of some optional components useful in the present invention may be outside the ranges listed herein.

The optional components, when incorporated into the composition, should be suitable for use in contact with human skin tissue without undue toxicity, incompatibility, instability, allergic response, and the like. The compositions of the present invention may include optional components such as anti-acne actives, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, and other useful skin care actives, which are described in further detail in U.S. application publication No. US2006/0275237A1 and US2004/0175347A1.

The Personal Care Product Council's *International Cosmetic Ingredient Dictionary and Handbook*, Thirteenth Edition, describes a wide variety of non-limiting cosmetic and pharmaceutical ingredients commonly used in the skin care industry, which are suitable optional components for use in the compositions of the present invention. Examples of these ingredient classes include: abrasives, absorbents, aesthetic components such as fragrances, pigments, colorings/colorants, essential oils, anti-caking agents, antifoaming agents, antimicrobials, binders, biological additives, buffering agents, bulking agents, chelating agents, chemical additives, colorants, cosmetic astringents, cosmetic biocides, denaturants, drug astringents, emollients, external analgesics, film formers or materials, opacifying agents, pH adjusters, preservatives, propellants, reducing agents, sequestrants, skin cooling agents, skin protectants, thickeners viscosity modifiers, vitamins, and combinations thereof.

F. Dermatologically Acceptable Carrier

The compositions of the present invention may also comprise a dermatologically acceptable carrier (which may be referred to as "carrier") for the composition. The phrase "dermatologically acceptable carrier", as used herein, means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. Non-limiting examples include simple solutions (e.g., aqueous, organic solvent, or oil based), emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

The aqueous phase typically comprises water. However, in other embodiments, the aqueous phase may comprise components other than water, including but not limited to water-soluble moisturizing agents, conditioning agents, anti-microbials, humectants and/or other water-soluble skin care actives. In one embodiment, the non-water component of the composition comprises a humectant such as glycerin and/or other polyols. However, it should be recognized that the composition may be substantially (i.e., less than 1% water) or fully anhydrous.

A suitable carrier is selected to yield a desired product form. Furthermore, the solubility or dispersibility of the components (e.g., extracts, sunscreen active, additional components) may dictate the form and character of the carrier. In one embodiment, an oil-in-water or water-in-oil emulsion is preferred.

Emulsions may further comprise an emulsifier. The composition may comprise any suitable percentage of emulsifier to sufficiently emulsify the carrier. Suitable weight ranges include from about 0.1% to about 10% or about 0.2% to about 5% of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and *McCutcheon's Detergents and Emulsifiers*, North American Edition, pages 317-324 (1986). Suitable emulsions may have a wide range of viscosities, depending on the desired product form.

The carrier may further comprise a thickening agent as are well known in the art to provide compositions having a suitable viscosity and rheological character.

II. Methods of Treatment

Various methods of treatment, application, regulation, or improvement may utilize the aforementioned compositions. In one embodiment, the method includes the step of identifying a hyperpigmented spot for improvement by the composition. The hyperpigmented spot may be identified by the user or a third party such as a dermatologist, cosmetician, or other caregiver. Identification may be done by visual inspection of the skin for hyperpigmented spots in need of treatment based on size and/or color. Identification may also be done by commercially available imaging devices such SIAscope® V (available from Astron Clinica, Ltd., UK) or the VISIA® Complexion Analysis system (available from Canfield Scientific, Inc., Fairfield, N.J.). Both devices are capable of collecting images of the skin and identifying hyperpigmented spots. In some instances, the method comprises the step of identifying a plurality of hyperpigmented spots for treatment by the composition.

Identification of the hyperpigmented spot may occur on any skin surface of the body. Skin surfaces of the most concern tend to be those not typically covered by clothing such as facial skin surfaces, hand and arm skin surfaces, foot and leg skin surfaces, and neck and chest skin surfaces (e.g., décolletage). In particular, identification of the hyperpigmented spot may be on a facial skin surface including the forehead, perioral, chin, periorbital, nose, and/or cheek skin surfaces.

The method may comprise the step of applying the composition to a hyperpigmented spot or spots, which may have been previously identified. Many regimens exist for the application of the composition to the hyperpigmented spot. The composition may be applied at least once a day, twice a day, or on a more frequent daily basis, during a treatment period. When applied twice daily, the first and second applications are separated by at least 1 to about 12 hours. Typically, the composition may be applied in the morning and/or in the evening before bed.

The treatment period is ideally of sufficient time to provide an improvement in the hyperpigmented spot. The improvement may be a detectable reduction in size of the hyperpigmented spot, lightening of the hyperpigmented spot (e.g., lighter in color), or decrease in melanin of the hyperpigmented spot. The treatment period may be at least about 1 week. The treatment period may last about 4 weeks or about 8 weeks. In certain embodiments, the treatment period will extend over multiple months (i.e., 3-12 months) or multiple years. In one embodiment the composition is applied to the hyperpigmented spot(s) at least once a day during a treatment period of at least about 4 weeks or at least about 8 weeks. In one embodiment the composition is applied to the hyperpigmented spot(s) twice a day during a treatment period of at least about 4 weeks or 8 weeks.

The step of applying the composition to the hyperpigmented spot may be accomplished by localized application. In reference to application of the composition, the term "localized", "local", or "locally" mean that the composition is delivered the targeted area (such as the hyperpigmented spot) while minimizing delivery to skin surface not requiring treatment. The composition may be applied and lightly massaged into the hyperpigmented spot. It is recognized that localized application does allow for a reasonable amount of the composition to be applied to areas adjacent the hyperpigmented spot (i.e., the composition is unlikely to be applied or to remain within the boundary of the hyperpigmented spot without some spreading). The form of the composition or the dermatologically acceptable carrier should be selected to facilitate localized application. While certain embodiments of the present invention contemplate applying a composition locally to a hyperpigmented spot, it will be appreciated that compositions of the present invention can be applied more generally or broadly to one or more facial skin surfaces to reduce the appearance of hyperpigmented spots within those facial skin regions.

In some embodiments, the composition may be delivered by a variety of applicators appropriate for localized and general application. Such applicators can include droppers, applicator wands, cotton swabs, or any other suitable device. Other suitable applicators include SH-0127 pen applicator available from Shya Hsin Plastic Works, Inc., Taiwan and either the Xpress Tip or liquid filled swab available from SwabPlus, Inc., China. The applicator may be configured to easily apply the composition to hyperpigmented spots having an approximate diameter between about 2 mm and about 10 mm and allowing for a dosed amount of the composition of between about 1 to about 50 uL/cm$^2$ or between about 1 to about 5 uL/cm$^2$. In another embodiment, the composition is applied to the one or more hyperpigmented spots and more generally to one or more facial skin surfaces contemporaneously (i.e., over a period of less than 30 minutes or, more typically, less than 5 minutes).

While some methods described herein contemplate applying the compositions of the present invention with an applicator, it will be appreciated that applicators are not required and the compositions of the present invention can also be applied directly by using one's finger or in other conventional manners.

In one embodiment, the method comprises the steps of applying a first composition comprising an effective amount of banyan tree serum fraction, lotus serum fraction, and clover serum fraction to a hyperpigmented spot or a plurality of hyperpigmented spots on a skin surface and of applying a second composition to the skin surface, before or after the first composition. The first and second compositions may be any compositions described herein; however, the second composition may optionally comprise an effective amount of the serum fractions present in the first composition. The second composition may comprise one or more tone agents, sunscreen actives, anti-inflammatory agents, or optional components. The first composition may be locally applied to the hyperpigmented spot or plurality of hyperpigmented spots. The second composition may be locally applied to the hyperpigmented spot or a plurality of hyperpigmented spots to which the first composition is applied or the second composition may be applied more generally to the skin surface including the hyperpigmented spots to which the first composition is applied. In certain embodiments, the skin surface is facial skin surface which include one or more of the forehead, perioral, chin, periorbital, nose, and cheek skin surfaces. In another embodiment, the first and second compositions are applied contemporaneously to at least the cheek, forehead, and chin/perioral skin surfaces. For general application to a skin surface and, particularly a facial skin surface, the dosed amount of the first or second composition may be between about 1 to about 50 uL/cm$^2$ per application (i.e., per single application to the skin surfaces).

Suitable methods may comprise any one or more of the abovementioned steps. All of the aforementioned steps are applicable to application, treatment, regulation, and/or improvement of both a single hyperpigmented spot as well as a plurality of hyperpigmented spots Likewise, the exemplary methods that follow are applicable to both a single hyperpigmented spot as well as a plurality of hyperpigmented spots.

One suitable method of improving the appearance of a hyperpigmented spot includes the step of topically applying a composition comprising an effective amount of banyan tree serum fraction, lotus serum fraction, and clover serum fraction to the hyperpigmented spot on a skin surface, wherein the composition is applied for a period of time sufficient for the serum fractions to improve the appearance of the hyperpigmented spot. Another suitable method of improving the appearance of hyperpigmented spots includes the steps of identifying a hyperpigmented spot on a skin surface, applying a composition comprising an effective amount of said serum fractions to the hyperpigmented spot on the skin surface, wherein the composition is applied for a period of time sufficient for the serum fractions to improve the appearance of the hyperpigmented spot.

Another suitable method is for improving the appearance of a post-inflammatory hyperpigmentation. The method may comprise the steps of identifying an area of post-inflammatory hyperpigmentation on a skin surface and of applying to the area said serum fractions and an anti-inflammatory active. An effective amount of said serum fractions may be applied at least daily for a period of time sufficient to improve the appearance of the area of post-inflammatory hyperpigmentation. Said serum fractions may be provided in a first composition and the anti-inflammatory agent provided in a second composition. Alternately, the said serum fractions and the anti-inflammatory agent may be provided in the same composition. The compositions may further comprise a sunscreen active, a skin tone agent, or combinations thereof.

EXAMPLES

Example 1

Exemplary Compositions

Table 1 sets forth non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

All examples may be used to treat or improve the appearance of one or more hyperpigmented spots. The present invention may further relate to a regimen involving the localized treatment for one or more hyperpigmented spots by a first composition (e.g., Examples A or B) and a more broad or general facial skin treatment by a second composition (e.g., Examples C or D), which can be applied before or after the localized treatment to improve skin tone across the face.

TABLE 1

Exemplary Compositions

| Component/% by wt. | Example A | Example B | Example C | Example D |
|---|---|---|---|---|
| *Ficus Benghalensis* (Banyan Tree) Flower/Leaf/Stem Juice (manufactured by Integrated Botanical Technologies) | 0.55 | 1.00 | 0.55 | 0.00 |
| *Nelumbo Nucifera* (Lotus) Flower/Leaf/Stem Juice (manufactured by Integrated Botanical Technologies) | 0.10 | 0.20 | 0.20 | 0.00 |
| *Trifolium Pratense* (Clover) Flower/Leaf/Stem Juice (manufactured by Integrated Botanical Technologies) | 0.10 | 0.20 | 0.20 | 0.00 |
| N-Acetylglucosamine | 0.00 | 0.00 | 2.00 | 0.00 |
| Hexamidine Diisethionate | 0.00 | 0.00 | 0.09 | 0.09 |
| Sepiwhite ™ (Undecylenoyl-phenylalanine, neutralized) (available from SEPPIC) | 0.00 | 0.00 | 0.50 | 0.50 |
| Sepigel 305 ™ (Polyacrylamide + C13-14 isoparaffin + laureth-7) (available from SEPPIC) | 0.00 | 0.00 | 2.00 | 2.00 |
| Dipotassium Glycyrrhizate | 0.00 | 0.10 | 0.10 | 0.30 |
| Hexamidine Diisethionate | 0.00 | 0.00 | 0.09 | 0.09 |
| Homosalate | 0.00 | 0.00 | 0.00 | 9.00 |
| Avobenzone | 0.00 | 0.00 | 0.00 | 3.00 |
| Octocrylene | 0.00 | 0.00 | 0.00 | 2.60 |
| Oxybenzone | 0.00 | 0.00 | 0.00 | 1.00 |
| Octisalate | 0.00 | 0.00 | 0.00 | 4.50 |
| Butylene Glycol (CAS No. 107-88-0) | 5.50 | 5.50 | 5.50 | 5.50 |
| Niacinamide (CAS No. 98-92-0) | 5.00 | 5.00 | 5.00 | 5.00 |

TABLE 1-continued

Exemplary Compositions

| Component/% by wt. | Example A | Example B | Example C | Example D |
|---|---|---|---|---|
| Glycerin (CAS No. 56-81-5) | 2.50 | 2.50 | 2.50 | 2.50 |
| DC 1503 Fluid ™ (available from DowCorning) | 2.50 | 2.50 | 2.50 | 2.50 |
| Lubrajel Oil ™ (available from Sederma) | 1.44 | 1.44 | 1.44 | 1.44 |
| Phenonip XB ™ (available from Clariant) | 1.25 | 1.25 | 1.25 | 1.25 |
| D-panthenol (CAS No. 81-13-0) | 1.00 | 1.00 | 1.00 | 1.00 |
| Tospearl 2000 ™ (Polymethylsilsesquioxane) (CAS No. 68554-70-1) (available from GE Silicones/Momentive) | 1.00 | 1.00 | 1.00 | 1.00 |
| DL-Alpha Tocopheryl Acetate (CAS No. 7695-91-2) | 0.50 | 0.50 | 0.50 | 0.50 |
| Prodew 400 ™ (available from Ajinomoto) | 0.50 | 0.50 | 0.50 | 0.50 |
| Pemulen TR-2 ™ (Acrylates/C10-30 Alkyl Acrylate Crosspolymer) (available from Noveon) | 0.25 | 0.25 | 0.25 | 0.25 |
| Polysorbate 20 (CAS No. 9005-64-5) | 0.25 | 0.25 | 0.25 | 0.25 |
| Sodium Metabisulfite (CAS No. 7681-57-4) | 0.25 | 0.25 | 0.25 | 0.25 |
| Allantoin (CAS No. 97-59-6) | 0.20 | 0.20 | 0.20 | 0.20 |
| Sodium Hydroxide (CAS No. 1310-73-2) (50% solution by weight in water) | 0.17 | 0.17 | 0.17 | 0.17 |
| Disodium EDTA (CAS No. 139-33-3) | 0.10 | 0.10 | 0.10 | 0.10 |
| Xanthan Gum (CAS No. 11138-66-2) | 0.05 | 0.05 | 0.05 | 0.05 |
| Sodium Hyaluronate (CAS No. 9067-32-7) | 0.01 | 0.01 | 0.01 | 0.01 |
| Water (CAS No. 7732-18-5) | QS | QS | QS | QS |
| TOTAL (% by weight of total composition) | 100.00 | 100.00 | 100.00 | 100.00 |

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared such as to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

Example 2

Melanin Synthesis Inhibition

Individual banyan tree, lotus, and clover serum fractions, as well as their blends, were evaluated according to the melanin synthesis assay described herein. A B16-F1 mouse melanoma cell line is employed in the assay. The B16-F1 cells are obtained from American Tissue Culture Collection, Virginia, USA. The cell culture medium used in the assay comprises 500 mL of Dulbecco's Modified Eagle's Medium (DMEM), 50 mL Fetal Bovine Serum (FBS), and 5 mL of penicillin-streptomycin liquid. B16-F1 cells that are cultured in this medium and grown to greater than 90% confluency synthesize melanin. While not intending to be bound by any theory, it is hypothesized that the melanin synthesis is stimulated by the culture medium and/or stress induced by growth to a high confluency. The DMEM and FBS can be obtained from American Tissue Culture Collection and the penicillin-streptomycin liquid can be obtained from Invitrogen, Inc., Calif., USA. Equipment used in the assay include a $CO_2$ incubator, such as a Forma Series Model 3110 by Therma Scientific, Massachusets, USA; a Hemocytometer, such as a Bright Line model by Hauser Scientific, Pennsylvania, USA; and a UV-Visible Spectrum Plate Reader, such as a SpectraMax250 from Molecular Devices, California, USA. The assay steps include:

1. Day 0—Cell Growth: Warm the cell culture medium to 37° C. and place 29 mL into a T-150 flask. Add approximately $1 \times 10^6$ of B16-F1 passage 1 mouse cells to the T-150 flask and incubate for 3 days at 37° C., 5% $CO_2$, 90% relative humidity, until about 80% confluency.
2. Day 3—Initiate a 96 Well Plate: At day 3, trypsinize the cells from the T-150 flask and determine the concentration of cells using the Hemacytometer. Initiate a 96 well plate with 2,500 cells per well in 100 uL of cell culture medium. Incubate the plate at 37° C., 5% $CO_2$, 90% relative humidity for 2 days until at least 20% to 40% confluent.
3. Day 5—Remove the cell culture medium from the plate and replace with fresh culture medium (100 uL per well). Add 1 uL of each test compound. Multiple dilution ratios may be tested in order to generate a dose response curve, wherein preferably three wells are treated with each dilution ratio. Controls comprise wells having the cell culture medium, B16-F1 cells, and the solvent (control #1); wells comprising the cell culture medium and the solvent (control #2); and optionally wells comprising the cell culture medium, solvent and [test compound] when necessary to control for the [test compound] background color (control #3).
4. Day 7—Measure Melanin Production: Cells should have a confluency greater than about 80%. If not, this data point is not used. Add 100 uL of a 0.75% sodium hydroxide solution to each well. Read the 96 well plate using the UV-Vis Plate Reader at 410 nm to optically measure the amount of melanin produced between wells that are treated with [test compound] and control wells that are not. Wells in which melanin is produced appear brownish in color. Wells in which little melanin is produced appear clear to light purple in color. Percentage of melanin synthesis inhibition is calculated by the following equation:

$$\frac{100 - [OD_{410\ Test\ Compound} - OD_{410\ Control\ \#2}]}{(OD_{410\ Control\ \#1} - OD_{410\ Control\ \#2})} \times 100$$

Where $OD_{410}$ is the Optical Density at 410 nm as measured by the UV-Vis Spectrum Plate Reader.
When Control #3 is used, the formula for percentage melanin synthesis inhibition is:

$$\frac{100 - [OD_{410\ Test\ Compound} - OD_{410\ Control\ \#3}]}{(OD_{410\ Control\ \#1} - OD_{410\ Control\ \#2})} \times 100$$

Using generally the assay outlined above, individual serum fractions and blends were analyzed for melanin synthesis in B16-F1 cells. The results obtained at two different test concentrations are set forth below as Example 2a and Example 2b.

Example 2a

| Serum Fraction | % Concentration | % Melanin Inhibition | T-test vs. Blend ($<0.05$ statistically significant) |
| --- | --- | --- | --- |
| Banyan Tree | 0.275 | 42 | 0.009291 |
| Clover | 0.05 | 16 | 0.007881 |
| Lotus | 0.05 | 1 | 0.001603 |
| Blend | 0.275 banyan tree + 0.05 clover + 0.05 lotus | 100 | |

Example 2b

| Serum Fraction | % Concentration | % Melanin Inhibition | T-test vs. Blend ($<0.05$ statistically significant) |
| --- | --- | --- | --- |
| Banyan Tree | 0.1375 | 0 | 0.001049 |
| Clover | 0.025 | 14 | 0.004098 |
| Lotus | 0.025 | 7 | 0.006366 |
| Blend | 0.275 banyan tree + 0.05 clover + 0.05 lotus | 63 | |

Example 3

Method of Treatment

A test subject topically applies composition A of Example 1 to the entire face once a day for 8 weeks. Photographs of the subject's face at week 0 and at week 8 are compared to show that the subject's overall facial skin tone improves (less hyperpigmented and more even) and hyperpigmented spots are lighter and smaller in size.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of improving the appearance of a hyperpigmented spot comprising the step of applying a first composition comprising:
   a. from 0.001% to 15% of banyan tree serum fraction, from 0.001% to 15% of lotus serum fraction, and from 0.001% to 15% of clover serum fraction blend, wherein the serum fractions do not contain any exogenous solvent; and
   b. a dermatologically acceptable carrier
   to a hyperpigmented spot on a skin surface, wherein the composition is applied for a period of time sufficient for the synergistic mixture to improve the appearance of the hyperpigmented spot.

2. The method of claim 1 wherein the skin surface is a facial skin surface.

3. The method of claim 2, wherein the first composition is applied to at least one of a forehead, perioral, chin, periorbital, nose, and cheek skin surfaces.

4. The method of claim 3, wherein the first composition is applied to each of the forehead, perioribital, perioral and cheek skin surfaces.

5. The method of claim 1, wherein the first composition is applied to at least once a day for at least about four weeks.

6. The method of claim 1, wherein the first composition is applied at least twice a day for at least about four weeks.

7. The method of claim 1, wherein the first composition is applied at least once a day for at least about eight weeks.

8. The method of claim 1, wherein the first composition is applied at least twice a day for at least about eight weeks.

9. The method of claim 1, wherein the improvement is a size reduction of the hyperpigmented spot.

10. The method of claim 1, wherein the improvement is increased lightness of the hyperpigmented spot.

11. The method of claim 1, wherein the improvement is a reduction in melanin of the hyperpigmented spot.

12. The method of claim 1, wherein the first composition further comprises a sunscreen active.

13. The method of claim 1, wherein the first composition further comprises an anti-inflammatory agent.

14. The method of claim 13, wherein the anti-inflammatory agent is selected from glycyrrhizic acid, glycyrrhizic acid salts, licorice extract, bisabolol, and combinations thereof.

15. The method of claim 1, wherein the first composition further comprises a skin tone agent.

16. The method of claim 15, wherein the skin tone agent is selected from the group consisting of vitamin B3 compounds, sugar amines, hexamidine compounds, salicylic acid, 1,3-dihydroxy-4-alkylbenzene, retinoids, and combinations thereof.

17. The method of claim 1, wherein the first composition is applied to a plurality of hyperpigmented spots for a period of time sufficient to improve the appearance of the plurality of hyperpigmented age spots.

18. The method of claim 17, wherein the improvement is a size reduction of the plurality of hyperpigmented spots.

19. The method of claim 17, wherein the improvement is increased lightness of the plurality of hyperpigmented spots.

20. The method of claim 17, wherein the improvement is a reduction in melanin of the hyperpigmented spot.

21. The method of claim 1, further comprising a step of applying a second composition to the skin surface.

22. The method of claim 21, wherein the second composition comprises an effective amount of banyan tree serum fraction, lotus serum fraction, and clover serum fraction.

23. The method of claim 21, wherein the second composition comprises a sunscreen active, an anti-inflammatory agent, or a skin tone agent.

24. The method of claim 23, wherein a skin tone agent is selected from a group consisting of vitamin B3 compounds, sugar amines, hexamidine compounds, salicylic acid, 1,3-dihydroxy-4-alkylbenzene, retinoids, and combinations thereof.

25. A method of improving the appearance of post-inflammatory hyperpigmentation, the method comprising the steps of:
a. identifying an area of post-inflammatory hyperpigmentation on a skin surface;
b. applying to the area from 0.001% to 15% of banyan tree serum fraction, from 0.001% to 15% of lotus flower serum fraction, and from 0.001% to 15% of red clover serum fraction, wherein the serum fractions do not contain any exogenous solvent and wherein the serum fractions are applied at least daily for a period of time sufficient to improve the appearance of the area of post-inflammatory hyperpigmentation; and
c. applying to the area an effective amount of an anti-inflammatory agent.

26. The method of claim 25, wherein the anti-inflammatory active is selected from glycyrrhizic acid, glycyrrhizic acid salts, licorice extract, bisabolol, and combinations thereof.

27. The method of claim 26, wherein the composition further comprises a sunscreen active, a skin tone agent, or combinations thereof.

28. The method of claim 27, wherein the skin tone agent is selected from the group consisting of vitamin B3 compounds, sugar amines, hexamidine compounds, salicylic acid, 1,3-dihydroxy-4-alkylbenzene, retinoids, and combinations thereof.

29. A composition for improving the appearance of hyperpigmented skin, comprising:
a. from 0.001% to 15% of banyan tree serum fraction, from 0.001% to 15% of lotus serum fraction, and from 0.001% to 15% of clover serum fraction, wherein the serum fractions do not contain any exogenous solvent; and
b. a dermatologically acceptable carrier.

* * * * *